(12) United States Patent
New

(10) Patent No.: US 7,303,762 B2
(45) Date of Patent: Dec. 4, 2007

(54) ABSORPTION ENHANCERS

(75) Inventor: Roger Randal Charles New, London (GB)

(73) Assignee: Axcess Limited, Jersey (GB)

( * ) Notice: Subject to any disclaimer, the term of this patent is extended or adjusted under 35 U.S.C. 154(b) by 112 days.

(21) Appl. No.: 10/398,228

(22) PCT Filed: Oct. 5, 2001

(86) PCT No.: PCT/GB01/04464

§ 371 (c)(1),
(2), (4) Date: Jul. 23, 2003

(87) PCT Pub. No.: WO02/28436

PCT Pub. Date: Apr. 11, 2002

(65) Prior Publication Data

US 2004/0028736 A1 Feb. 12, 2004

(30) Foreign Application Priority Data

Oct. 6, 2000 (GB) .............................. 0024543.1

(51) Int. Cl.
*A61K 9/48* (2006.01)
*A61K 38/00* (2006.01)

(52) U.S. Cl. .................. 424/463; 424/452; 424/9.1; 514/12; 514/946; 530/350

(58) Field of Classification Search .......... 530/350; 514/2, 12, 946; 424/9.1, 463, 452
See application file for complete search history.

(56) References Cited

U.S. PATENT DOCUMENTS 4,804,541 A * 2/1989 Nichols .................. 424/449
5,196,184 A 3/1993 Burghart et al.
6,485,706 B1 * 11/2002 McCoy et al. ........... 424/45

FOREIGN PATENT DOCUMENTS

EP 0 371 010 A 5/1990
WO WO 93 06854 A 4/1993

OTHER PUBLICATIONS

Asada et al., *J Pharm Sci* 84 682-7 (1995) "Absorption characteristics of chemically-modified insulin derivatives with various fatty acids in the small and large intestine."
Bai et al., *Crit Rev Ther Drug Carrier Syst* 12 339-71 (1994) "Targeting of peptide and protein drugs to specific sites in the oral route."
Fagerholm et al., *J Pharm Pharmacol* 50 467-73 (1998) "The effect of a drug delivery system consisting of soybean phosphatidyl choline and medium chain monoacyl glycerol on the intestinal permeability of hexarelin in the rat."
Morishita et al., *Biol Pharm Bull* 16 68-72 (1993) "Site-dependent effect of aprotinin, sodium caprate, Na2EDTA and sodium glycholate on intestinal absorption of insulin."
Saunders et al., *Gut* 16 543-8 (1975) "Regional differences in oxalate absorption by rat intestine: evidence for excessive absorption by the colon in steatorrhoea."
Wang et al., *Biol Pharm Bull* 17 1399-403 (1994) "Mechanism of gastrointestinal absorption of glycyrrhizin in rats."
Yamamoto et al., *J Pharm Pharmacol* 49 1057-61 (1997) "Effects of different absorption enhancers on the permeation of ebiratide, an ACTH analogue, across intestinal membranes."

* cited by examiner

*Primary Examiner*—Chih-Min Kam
(74) *Attorney, Agent, or Firm*—Nixon & Vanderhye P.C.

(57) ABSTRACT

The invention relates to the use of hydrophilic aromatic alcohols to enhance the uptake of molecules, including biologically active macromolecules, into the body across the intestinal wall from the lumen of the gut; to compositions for oral administration which consists of an enteric capsule capable of withstanding transit through the stomach, containing a mixture comprising: (a) an active principal, and (b) a hydrophilic aromatic alcohol absorption enhancer; and to the user of the composition in medical treatment and diagnosis.

32 Claims, No Drawings

ABSORPTION ENHANCERS

This application is the US national phase of international application PCT/GB01/04464 filed 5 Oct. 2001, which designated the US.

The present invention relates to the use of hydrophilic aromatic alcohols to enhance the uptake of molecules, including biologically active macromolecules, into the body across the intestinal wall from the lumen of the gut. In particular the present invention relates to novel compositions for oral administration comprising an active principal to be absorbed across the intestinal wall.

Hydrophilic aromatic alcohols such as phenoxyethanol, phenyl ethanol and benzyl alcohol, have been employed in pharmaceutical practice for many years as solvents and plasticisers, and have a low toxicity profile when administered via various routes, including the oral route.

The applicant has found that hydrophilic aromatic alcohols such as phenoxyethanol and related compounds including phenyl ethanol and benzyl alcohol, have a range of actions on intestinal cells. One of which effects is that, when present in relatively high local concentration, aromatic alcohols transiently increase the permeability of a barrier layer of intestinal cells. It is postulated that this is due to the opening of the tight junctions between these cells creating pores through which even large molecules (macromolecules) can pass by diffusion.

Based on the finding that an increase in the permeability of a barrier layer of intestinal cells is only seen at relatively high local concentrations of hydrophilic aromatic alcohol, the applicant's research has shown that a solution of hydrophilic aromatic alcohol co-administered orally (as an elixir) with a detectable molecule produces no enhancement of uptake. It is postulated that this is because, before it reaches the absorption site (in the intestine), the hydrophilic alcohol is rapidly diluted in the gastrointestinal tract to a concentration below which it cannot exert its effect. In addition, the molecules whose uptake one is seeking to elicit will also be diluted out before the intestine is reached.

The invention provides a composition for oral administration which consists of an enteric capsule capable of withstanding transit through the stomach, containing a mixture comprising:
(a) an active principal, and
(b) a hydrophilic aromatic alcohol absorption enhancer.

The invention also provides the use, in a composition for oral administration, of a hydrophilic aromatic alcohol as an enhancer for the absorption of molecules across the intestinal wall.

In a further embodiment the invention provides the use of a hydrophilic aromatic alcohol in the manufacture of a medicament (pharmaceutical composition) containing an active principal, in order to enhance absorption of the active principal across the intestinal wall into the human or animal body.

Aromatic alcohols suitable for use as absorption enhancers according to the invention are hydrophilic molecules containing at least one aromatic ring and at least one hydroxyl group. Preferably the hydrophilic aromatic alcohol does not contain a carboxylic acid group, still more preferably the hydrophilic aromatic alcohol does not contain a carboxylic acid group or an amide group. Preferred hydrophilic aromatic alcohols for use in the invention have a 5- or 6-membered aromatic, alicyclic or heterocyclic ring which is unsubstituted or substituted by one or more halogen atoms or $C_{1-4}$ alkyl, $C_{1-4}$ alkoxy, $C_{1-4}$ alkylthio or $C_{2-4}$ alkenyl groups and have at least one hydroxyl group either attached directly to the ring or to the substituent groups on the ring. Preferably, there are no hydroxyl groups attached directly to the ring of the hydrophilic aromatic alcohol. In preferred embodiments of the invention the hydrophilic aromatic alcohol is a liquid at normal body temperature (37° C.). Examples of the most preferred hydrophilic aromatic alcohols for use in the invention include phenoxyethanol, benzyl alcohol, phenyl ethanol and analogues, homologues and derivatives thereof.

The molecules and active principals falling within the scope of the invention include all molecules capable of having a beneficial effect when absorbed into the human or animal body through the intestinal wall. The beneficial effect may be, for example, therapeutic, cosmetic or preventative such as prophylactic or contraceptive. The molecules and active principals may be small molecules or macromolecules and can be of natural (biological), synthetic or semi-synthetic origin.

Examples of small molecules and small molecule active principals include any molecules of less than 3000 Da, preferably less than 2000 Da and most preferably less than 1000 Da which may have a beneficial effect in treating disorders of the blood, kidney, brain, liver, bone, skin, hair follicles, joints, eye, ear, nose and throat, alimentary tract, reproductive organs, connective tissue or cardiovascular, respiratory, endocrine, muscular, urinary, immune or nervous systems, including molecules which are effective in the treatment of cancer, infections, geriatric diseases, epilepsy, Parkinson's disease, Alzheimers disease, CJD, sleeping disorders, migraine, diabetes, osteoporosis, inflammation, which are employed to overcome the effects of poisoning, for detoxification, for correction of water, electrolyte or acid balance disturbances, for pain relief, for adjustment of body weight, for control of appetite, anaesthesia, or treatment of psychiatric diseases or which may bring about a beneficial change in the status of the immune system. Such molecules may include vitamins, hormones, contraceptives, fertility drugs, tonics, antidepressants, anticancer agents, anti-coagulants, antibiotics such as antibacterial, antiparasitics, antifungal agents and antiviral, receptor agonists and antagonists, enzyme inhibitors, enzyme promoters, DNA intercalating agents, DNA binding agents, antihistamines, immunosuppressants, immunostimulants, or other drugs which are able to counteract the toxic side-effects of the molecules cited above.

Macromolecules are preferably defined as molecules having a molecular weight of over 1000 Da, preferably over 2000 Da and most preferably over 3000 Da.

Examples of macromolecules, including macromolecular active principals, include:

1. Polypeptides and proteins such as insulin; calcitonin; growth hormone; growth hormone releasing factors; galanin; parathyroid hormone; blood clotting proteins such as kinogen, prothombin, fibrinogen, Factor VII, Factor VIII of Factor IX; erythropoeitins and EPO mimetics; colony stimulating factors including GCSF and GMCSF; platelet-derived growth factors; epidermal growth factors; fibroblast growth factors; transforming growth factors; GLP-1; GAG; cytokines; insulin-like growth factors; bone- and cartilage-inducing factors; neurotrophic factors; interleukins including IL-1, IL-2, IL-3, IL-4, IL-5, IL-6, IL-7, IL-8, IL-9, IL-10, IL-11, IL-12; interferons including interferon gamma, interferon β-1a, interferon alphas; TNF alpha; TNF beta; TGF-beta; cholera toxin A and B fragments; *E. coli* enterotoxin A and B fragments; secretin; enzymes including superoxide dismutase, catalase, adenosine deaminase, thymidine kinase, cytosine deaminase, proteases, lipases, carbohydrases, nucleotidases, polymerases, kinases and phosphatases; transport or binding proteins especially those which bind and/or transport a vitamin, metal ion, amino acid or lipid or lipoprotein such as cholesterol ester transfer protein, phospholipid transfer protein, HDL binding protein; connective tissue proteins such as a collagen, elastin or fibronectin; a muscle protein such as actin, myosin, dystrophin, or minidystrophin; a neuronal, liver, cardiac, or adipocyte protein; a cytotoxic protein; a cytochrome; a protein which is able to cause replication, growth or differentiation of cells; a signalling molecule such as an intra-cellular signalling protein or an extracellular signalling protein (eg hormone); trophic factors such as BDNF, CNTF, NGF, IGF, GMF, AFGF, bFGF, VEGF, NT3, T3 and HARP; apolipoproteins; antibody molecules; receptors in soluble form such as T-cell receptors and receptors for cytokines, interferons or chemokines; proteins or peptides containing antigenic epitopes and fragments; and derivatives, conjugates and sequence variants of any of the above. These and other proteins may be derived from human, plant, animal, bacterial or fungal sources, and extracted either from natural sources, prepared as recombinants by fermentation or chemically synthesised.

2. Polynucleotides such as long-chain linear or circular single-, double- or triple-stranded DNA, single-, double- or triple-stranded RNA, oligonucleotides such as antisense DNA or RNA, and analogues thereof including PNA and phosphothioate derivates. In one embodiment it is preferred that the polynucleotides used in the invention contain a CpG motif. The coding sequence of the polynucleotide may encode a therapeutic product, in particular the coding sequence may encode an extracellular protein (e.g. a secreted protein); an intracellular protein (e.g. cytosolic, nuclear or membrane protein); a protein present in the cell membrane; a blood protein, such as a clotting protein (e.g. kinogen, prothrombin, fibrinogen factor VII, factor VIII or factor IX); an enzyme, such as a catabolic, anabolic gastrointestinal, metabolic (e.g. glycolysis or Krebs cycle), or a cell signalling enzyme, an enzyme which breaks down or modifies lipids, fatty acids, glycogen, amino acids, proteins, nucleotides, polynucleotides (e.g. DNA or RNA) or carbohydrate (e.g. protease, lipase or carbohydrase), or a protein modifying enzyme, such as an enzyme that adds or takes chemical moieties from a protein (e.g. a kinase or phosphatase); a transport or binding protein (e.g. which binds and/or transports a vitamin, metal ion, amino acid or lipid, such as cholesterol ester transfer protein, phospholipid transfer protein or an HDL binding protein); a connective tissue protein (e.g. a collagen, elastin or fibronectin); a muscle protein (e.g. actin, myosin, dystrophin or mini-dystrophin); a neuronal, liver, cardiac or adipocyte protein; a cytotoxic protein; a cytochrome; a protein which is able to cause the replication, growth or differentiation of cells; a protein which aids transcription or translation of a gene or regulates transcription or translation (e.g. a transcription factor or a protein that binds a transcription factor or polymerase); a signalling molecule, such as an intracellular or extracellular signalling molecule (e.g. a hormone); an immune system protein such as an antibody, T cell receptor, MHC molecule, cytokine (e.g IL-1, IL-2, IL-3, IL-4, IL-5, IL-6, IL-7, IL-8, IL-9, IL-10, TNF-α, INF-β, TGF-β), an interferon (e.g. IFN-α, IFN-β, IFN-γ), chemokine (e.g. MIP-1α, MIP-1β, RANTES), an immune receptor (e.g. a receptor for a cytokine, interferon or chemokine, such as a receptor for any of the above-mentioned cytokines, interferons or chemokines) or a cell surface marker (e.g. macrophage, T cell, B cell, NK cell or dendritic cell surfacemarker)(eg. CD 1, 2, 4, 5, 6, 7, 8, 16, 18, 19, 28, 40, or 45; or a natural ligand thereof), a trophic factor (e.g. BDNF, CNTF, NGF, IGF, GMF, AFGF, bFGF, VEGF, NT3, T5, HARP) or an apolipoprotein; a tunour suppressor (e.g. p53, Rb, Rap1A, DCC or k-rev); or a suicide protein (thymidine kinase or cytosine deaminase). The proteins and peptides encoded by the polynucleotides useful in the invention may be immunogenic i.e. contain an antigen specific to the activity of the protein against which antibodies are generated by the immune system.

The polynucleotide may have control sequences operably linked to the coding sequence. The control sequences may typically be those of any eukaryote or of a virus which infects such eukaryotes. The polynucleotide may comprise an origin of replication.

The polynucleotides may be chemically modified. This may enhance their resistance to nucleases or may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

The polynucleotide suitable for use in the invention is preferably in a form in which it is substantially free of or associated with cells or with cellular, prokaryotic, eukaryotic, nuclear, chromatin, histone or protein material. It may be in substantially isolated form, or it may be in substantially purified form, in which case it will generally comprise more than 90%, e.g. (more than or at least) 95%, 98% or 99% of the polynucleotide or dry mass in the preparation. Thus the polynucleotide may be in the form of 'naked DNA'.

3. Polysaccharides such as heparin, low-molecular weight heparin, polymannose, cyclodextrins and lipopolysaccharide.

4. Any or all of the above either separately or in combination with each other (for example in the form of a heteroconjugate), or with additional agents.

In preferred embodiments of the invention the molecules/active principals are macromolecules/macromolecular active principals. In the most preferred embodiments of the invention the molecule/active principal to be absorbed is selected from calcitonins, insulin, low molecular weight heparin, and polymannose.

The enteric capsule used in the composition of the invention is chosen appropriately to withstand the natural condition of the stomach and to become permeable at the desired location in the intestine. This is preferably determined by the pH conditions which modulate along the length of the intestine. In the composition of the invention it is preferred that the enteric capsule becomes permeable and releases its contents at a pH from 5.5 to 7 preferably 5.5 to 6.5. Most preferably, the enteric coated capsule becomes permeable and releases its contents in the jejunal region of the mammalian gastrointestinal tract.

Suitable enteric coatings are well known in the art and include polymethacrylates such as those selected from the L and S series of Eudragits in particular Eudragits L12.5P, L12.5, L100, L100-55, L30D-55, S12.5P, S12.5 and S100. Selection of an appropriate coating for the capsule, which is preferably a gelatine capsule, can readily be made by the person skilled in the art based on their knowledge and the available literature supporting the Eudragit products.

The amount of aromatic alcohol and macromolecular active principal in the compositions of the invention, is chosen so as to achieve, at the intestinal cell barrier layer (intestinal wall), an effective concentration of aromatic alcohol so as to cause enhanced absorption in the co-presence of a suitable amount of the active principal which, when absorbed, will exert its normal beneficial effect. The practitioner of the invention would select the amounts of the aromatic alcohol and active principal on the basis of the amount (for example, blood concentration level) of the active principal concerned which is necessary for therapeutic effectivity. For example, the weight ratio of aromatic alcohol to active principal in the mixture contained in the capsule may be from 1000:1 to 1:3, preferably 750:1 to 3:1 and most preferably 600:1 to 9:1.

In the compositions of the invention it is preferred that the mixture contained in the capsule (not including the capsule itself) comprises at least 25%, preferably at least 50% and most preferably at least 75% by weight of the aromatic alcohol. In general it is preferred that the hydrophilic aromatic alcohol is used as an absorption enhancer in compositions which comprise at least 25%, more preferably at least 50% and most preferably at least 75% of the hydrophilic aromatic alcohol by weight of the entire composition.

The absolute amount of the macromolecular active principal would be selected on the basis of the dosage of the substance required to exert the normal beneficial effect with respect to the dosage regimen used and the patient concerned. Determination of these amounts fall within the mantle of the practitioner of the invention.

In the composition for oral administration it is preferred that the contents of the capsule comprises a suitable amount of the active principal to achieve its normal therapeutic effect. For example, the composition may contain from 0.05 to 50%, preferably from 0.1 to 25%, more preferably from 0.1 to 10% by weight of the active principal based on the weight of the capsule contents (not including the capsule itself).

The mixture contained in the capsule in the composition of the invention may also-contain one or more solubilising agents. These are preferably amphiphiles such as those mentioned below. Amphiphiles are preferably used in the compositions of the invention in amounts up to 25%, preferably up to 20% and more preferably up to 15% by weight of the capsule contents (not including the capsule itself).

The composition of the invention may further comprise one or more other absorption enhancer compounds, for example, bile salts, medium chain fatty acids and medium chain monoglycerides. In preferred embodiments of the invention the composition does not contain glycyrrhizinic acid or its salts as an absorption enhancer. In more preferred embodiments of the invention the hydrophilic aromatic alcohol is the sole absorption enhancer component.

The composition of the invention may optionally further comprise any conventional additive used in the formulation of pharmaceutical products including, for example, antioxidants, anti-microbials, suspending agents, fillers, diluents, viscosity regulators, plasticisers and acidity regulators (particularly those adjusting the intestinal milieu to between 7 and 7.5).

In the composition of the invention the mixture contained in the capsule which comprises the aromatic alcohol absorption enhancer and active principal is preferably substantially anhydrous. In more preferred embodiments of the invention the entire composition is substantially anhydrous. Substantially anhydrous in the context of this invention means less than 5%, preferably less than 1% and more preferably less than 0.5% water by weight of the mixture.

The compositions of the invention can, depending on the active principal used therein, be used in the treatment of a variety of conditions and diseases of the human or animal body by therapy or, alternately, can be used to introduce macromolecules essential for the diagnosis of diseases and conditions within the human or animal body. The compositions of the invention are preferably pharmaceutical or cosmetic compositions.

In preferred compositions of the invention the mixture contained in the capsule is a liquid which is either in the form of a solution or a microparticulate dispersion. That is to say the active principal(s) for absorption are incorporated into the hydrophilic aromatic alcohol either in the form of a solution or as a microparticulate dispersion.

The compositions of the invention are preferably produced by preparing a substantially anhydrous mixture of the active principal and the hydrophilic aromatic alcohol and then either filling pre-coated enteric capsules with the mixture or filling uncoated capsules with the mixture and then coating them with an appropriate polymer mixture to achieve the desired permeability properties.

In many cases, a clear solution of the active principal in the enhancer may be achieved simply by mixing the molecule and hydrophilic aromatic alcohol together. In other cases, particularly where the active principal is a macromolecule, solubility of the active principal in the hydrophilic aromatic alcohol may be enhanced by mixing the active principal with the hydrophilic aromatic alcohol in conjunction with one or more solubilising agents such as amphiphiles.

The suitability of particular amphiphiles may vary according to the active principal to be incorporated, but as a general rule amphiphiles with polyoxyethylated headgroups, hydroxylated amphiphiles or polymeric amphiphiles such as polyvinyl pyrrolidone are preferred. The amphiphile may be dissolved in the aromatic alcohol before addition of the active principal. As an alternative, the amphiphile and active principal may be co-dissolved in an aqueous phase, the water removed, for example, by lyophilisation, spray-drying or filtration of a precipitate, and the resulting water-free complex then dissolved in the aromatic alcohol.

Amphiphiles preferred for use in this invention are: polyoxyethylene-containing surfactants with a high HLB such as polyoxyethylene 40 monostearate, polyoxyethylene 20 cetyl ether, polysorbate 80; block co-polymers such as Lutrol F68; bile salts such as chelate, glycholate, deoxycholate, glycodeoxycholate, chenodeoxycholate, taurodeoxycholate, ursodeoxycholate and fusidate; and amphiphilic polymers such as polyvinyl pyrrolidone.

An alternative method for enhancing the solubility of active principal in the hydrophilic aromatic alcohol of the invention is to treat the active principal prior to incorporation with a suitable solubilising agent, for example, chains of polyethylene glycol.

In a third method for enhancing solubility of the active principals, a stable dispersion of active principal in the aromatic alcohol may be prepared by prior dissolution of the active principal in high concentration in a hydrophilic phase, such as the solubilising agent polyethylene glycol or propanediol, followed by addition to the aromatic alcohol with vigorous mixing.

In some cases, the above methods may yield dispersions rather than solutions, which may also have the desired efficacy in enhancing the uptake of the macromolecule incorporated, particularly if that macromolecule is in a form which is readily dissoluble in an aqueous phase.

In this invention the absorption of macromolecules (macromolecular active principal) is enhanced if the absorption is more rapid over a prespecified time period or more complete. In order to confirm that any particular hydrophilic aromatic alcohol fitting the description is suitable for use as an absorption enhancer, it is possible to carry out a test experiment, for example, the test described below in Example 11 in which radioactive polyethylene glycol or other suitable substance is dissolved in the material to be tested, and the solution is administered to animals, followed by sampling of blood to determine whether enhancement of uptake into the blood stream has indeed occurred.

The following Examples serve to illustrate the present invention and should not be construed as limiting.

EXAMPLE 1

Bovine insulin was formulated with benzyl alcohol at a concentration of 1000 iu per gram of benzyl alcohol as follows, and filled into hard gelatin capsules.

1. In a 20 ml glass screw-capped scintillation vial, weigh out 1.785 g of sodium ursodeoxycholate, then add 10 g of distilled water. Flush with nitrogen, cap tightly, seal with parafilm, and incubate at 37° C. to give a clear solution.
2. In a 20 ml glass screw-capped scintillation vial, weigh 100 mg of insulin, then add with gentle mixing, 3.3 g of sodium ursodeoxycholate solution from step 1, followed by 2.8 ml of distilled water. Flush with nitrogen, cap well and mix at 37° C. with shaking until dissolution occurs (about one hour).
3. Split the solution obtained in step 2 above into two equal aliquots by transferring 3.1 g of the solution into a fresh scintillation vial. Freeze the contents of both vials in liquid nitrogen and lyophilise overnight.
4. The following day, add to each of the dry residues in the vials obtained in step 3 above, 1.4 g of benzyl alcohol, flush with nitrogen, cap well and mix on a roller mixer at room temperature until a clear solution is obtained.
5. Dispense 242.9 mg of the insulin solution obtained in step 4 above into each of 12 hard gelatin capsules (size 4).

EXAMPLE 2

Bovine insulin was formulated with phenoxy ethanol at a concentration of 1000 iu per gram of phenoxy ethanol in an identical manner to that described in Example 1.

EXAMPLE 3

Low molecular weight heparin was formulated with benzyl alcohol at a concentration of 62.5 mg per gram of benzyl alcohol as follows, and then filled into hard gelatin capsules.

1. Weigh out 3.00 g of polyvinyl pyrrolidone into a 20 ml glass scintillation vial, and add 20 ml of distilled water. Cap well and mix on a roller mixer until dissolution is complete
2. Into a fresh 20 ml glass vial weigh out 1.200 g of low molecular weight heparin and then add 16.0 g of the solution obtained in step 1 above. Cap well and mix on a roller mixer until dissolution is complete.
3. Transfer 4.3 g of the solution obtained in step 2 above into each of three fresh 20 ml glass vials.
4. To each of vials 1 to 4 obtained in steps 2 and 3 above add 1 ml of distilled water and mix well, then freeze all vials in liquid nitrogen and lyophilise overnight.
5. The following day, add 4.80 g of benzyl alcohol to each of the vials. Mix on a roller mixer until dissolution is complete.
6. Fill each of twenty size 0 hard gelatin capsules with 950 mg of solution from the vials obtained in step 5 above.

EXAMPLE 4

Low molecular weight heparin was formulated with phenoxy ethanol at a concentration of 62.5 mg per gram of phenoxy ethanol in an identical manner to that described in example 3.

EXAMPLE 5

Salmon calcitonin was formulated with benzyl alcohol at a concentration of 2 mg per gram of benzyl alcohol as follows, and then filled into hard gelatin capsules.

1. Weigh out 100 mg of polyvinyl pyrrolidone into an 8 ml glass vial, and add 0.9 g of distilled water. Cap well and mix on a roller mixer until dissolution is complete.
2. Into a fresh 8 ml glass vial, weigh out 20 mg of salmon calcitonin and then add 0.8 g of the solution obtained in step 1 above. Cap well and mix on a roller mixer until dissolution is complete.
3. Transfer 0.41 g of the solution obtained in step 2 above into a fresh 8 ml glass vial.
4. Freeze the vials obtained in steps 2 and 3 above in liquid nitrogen and lyophilise overnight.
5. The following day, add 5.0 g of benzyl alcohol to each vial and mix on a roller mixer until dissolution is complete.
6. Fill each of eighteen size 2 hard gelatin capsules with 505 mg of the solution from vial 1 obtained in step 5 above.

EXAMPLE 6

Salmon calcitonin was formulated with phenoxy ethanol at a concentration of 2 mg per gram of phenoxy ethanol in an identical manner to that described in example 5.

EXAMPLE 7

14C-labelled polyethylene glycol, with a molecular weight of 4,000 (14C-PEG 4,000) was formulated with benzyl alcohol at a concentration of 25 µCi per ml as follows.

1. Transfer 200 µl of 14C-PEG 4,000 in aqueous solution (nominal activity 10 µCi) to a 2 ml glass vial, and lyophilise overnight in a centrifugal lyophiliser to remove all the water.
2. To the contents of the vial add 400 µl of benzyl alcohol, cap the vial, vortex mix the liquid for 30 seconds, then leave on a roller mixer at room temperature for 30 minutes.

EXAMPLE 8

14C-labelled polyethylene glycol, with a molecular weight of 4,000 (14C-PEG 4,000) was formulated with phenoxy ethanol at a concentration of 25 µCi per ml in an identical fashion to that described in example 7.

EXAMPLE 9

Formulations prepared as described in examples 1 and 2 were administered (one capsule per animal) directly to the intestine of conscious pigs (40 to 60 kg) via an in-dwelling stoma implanted surgically in the jejunum. Before and after administration, at the intervals shown, blood samples were taken for analysis of blood glucose levels. As a control, capsules containing 200 iu of unformulated insulin were also administered intra-jejunally. Falls in blood glucose over time for each group (+s.d.) are shown in Table 1 below. The marked falls in glucose for the formulated insulin, but not for the control, demonstrate the efficacy of hydrophilic alcohols such as benzyl alcohol and phenoxyethanol as permeation enhancers.

TABLE 1

Changes in plasma glucose (mmol/l)

| Time in minutes | Example 1 (insulin in benzyl alcohol) | Example 2 (insulin in phenoxy ethanol) | Control (unformulated insulin) |
|---|---|---|---|
| −10 | 0.00 | 0.00 | 0.00 |
| 15 | −0.80 + 0.40 | −0.80 + 0.77 | 0.01 + 0.24 |
| 30 | −2.02 + 1.77 | −1.78 + 1.50 | −0.05 + 0.21 |
| 45 | −2.22 + 1.47 | −1.69 + 1.40 | −0.06 + 0.17 |
| 60 | −1.92 + 1.31 | −1.06 + 1.18 | −0.32 + 0.23 |
| 90 | −1.41 + 1.06 | −0.71 + 0.83 | −0.17 + 0.21 |
| 120 | −1.17 + 0.66 | −0.72 + 0.68 | −0.22 + 0.32 |
| 180 | −0.90 + 0.50 | −0.68 + 0.46 | −0.13 + 0.21 |
| 240 | −0.84 + 0.58 | −0.79 + 0.74 | −0.34 + 0.32 |

EXAMPLE 10

Formulations prepared as described in examples 5 and 6 were administered (one capsule per animal) directly to the intestine of conscious pigs (40 to 60 kg) via an in-dwelling stoma implanted surgically in the jejunum. Before and after administration, at the intervals shown, blood samples were taken for analysis of calcium levels. Falls in plasma calcium and plasma calcitonin over time for each group (+s.d.) are shown in Tables 2 and 3 respectively. The marked falls in calcium for the formulated calcitonin demonstrate the efficacy of hydrophilic alcohols such as benzyl alcohol and phenoxyethanol as permeation enhancers.

TABLE 2

Changes in plasma calcium (mmol/l)

| Time in minutes | Example 5 (calcitonin in benzyl alcohol) | Example 6 (calcitonin in phenoxy ethanol) |
|---|---|---|
| −10 | 0.00 | 0.00 |
| 15 | −0.16 + 0.07 | −0.08 + 0.11 |
| 30 | −0.35 + 0.10 | −0.36 + 0.10 |
| 45 | −0.55 + 0.08 | −0.53 + 0.11 |
| 60 | −0.66 + 0.09 | −0.64 + 0.12 |
| 120 | −0.80 + 0.25 | −0.88 + 0.12 |
| 180 | −0.66 + 0.41 | −0.85 + 0.18 |
| 240 | −0.38 + 0.30 | −0.45 + 0.31 |
| 360 | −0.11 + 0.16 | −0.05 + 0.12 |

TABLE 3

Changes in plasma calcitonin (pg/ml)

| Time in minutes | Example 5 (calcitonin in benzyl alcohol) | Example 6 (calcitonin in phenoxyethanol) |
|---|---|---|
| 0 | 0 | 0 |
| 15 | 98.66 + 124.28 | 98.73 + 94.74 |
| 30 | 75.23 + 69.01 | 93.25 + 76.12 |
| 45 | 29.30 + 41.50 | 103.89 + 117.05 |
| 60 | 21.69 + 28.47 | 45.89 + 46.64 |
| 120 | 0 | 0 |

EXAMPLE 11

40 µl of the formulations described in examples 7 and 8 were administered by injection directly into the duodenum of anaesthetised rats (~200 g). Blood samples were removed at the intervals shown before and after administration, and analysed for radioactivity by scintillation counting. As a control, 14C-PEG 4,000 in phosphate-buffered saline was administered into the duodenum, in the absence of either benzyl alcohol or phenoxyethanol. Changes in blood radioactivity over time for each group (+s.d.) are shown in Table 4 below. Increased levels of radioactivity in the bloodstream after administration of the formulated PEG, compared with the control, demonstrate the ability of hydrophilic alcohols such as benzyl alcohol and phenoxyethanol to act as permeation enhancers.

TABLE 4

Changes in plasma radioactivity (dpm/150 µl)

| Time in minutes | Example 7 (PEG in benzyl alcohol) | Example 8 (PEG in phenoxy ethanol) | Control (unformulated PEG) |
|---|---|---|---|
| 0 | 0.1 + 0.13 | 0.3 + 0.59 | 0.7 + 0.93 |
| 30 | 14.1 + 5.87 | 20.6 + 9.39 | 4.7 + 1.84 |
| 60 | 8.9 + 3.71 | 8.0 + 2.61 | 4.1 + 1.56 |
| 90 | 6.6 + 2.75 | 5.4 + 1.69 | 4.2 + 2.36 |
| 120 | 6.2 + 2.57 | 4.8 + 3.86 | 3.3 + 1.32 |
| 150 | 5.9 + 3.68 | 5.9 + 5.72 | 2.7 + 1.44 |
| 180 | 5.5 + 2.86 | 6.1 + 9.50 | 1.9 + 0.57 |

EXAMPLE 12

$^{14}$C-labelled polyethylene glycol, with a molecular weight of 4,000 ($^{14}$C-PEG 4,000) was formulated with benzyl alcohol at a concentration of 800 µCi per ml as follows.

1. Transfer 800 µl of $^{14}$C-PEG 4,000 in aqueous solution (nominal activity 40 µCi) to a 2 ml glass vial, and lyophilise overnight in a centrifugal lyophiliser to remove all the water.

2. To the contents of the vial add 50 µl of benzyl alcohol, cap the vial, vortex mix the liquid for 30 seconds, then leave on a roller mixer at room temperature for 30 minutes.

EXAMPLE 13

$^{14}$C-labelled polyethylene glycol, with a molecular weight of 4,000 ($^{14}$C-PEG 4,000) was formulated with phosphate-buffered saline at a concentration of 800 µCi per ml in an identical fashion to that described in Example 12.

EXAMPLE 14

5 µl of the formulations described in Examples 12 and 13 were administered by application directly under the tongue of anaesthetised rats (~200 g). Blood samples were removed at the intervals shown below and after administration, and analysed for radioactivity by scintillation counting. Changes in blood radioactivity over time for each group (+s.d.) are shown in Table 5 below. As can be seen, in contrast to administration via the intestinal route, a formulation of benzyl alcohol applied sub-lingually displays no enhancement in uptake of macromolecule into the bloodstream. This observation illustrates the generally accepted fact that success in adminstration of materials via one route does not indicate or guarantee likelihood of success via a different route.

TABLE 5

Changes in plasma radioactivity (dpm/150 µl)

| Time in minutes | Example 12 (PEG in benzyl alcohol) | Example 13 (PEG in phosphate buffered saline) |
|---|---|---|
| 0 | 1.4 ± 1.9 | 1.6 ± 1.9 |
| 30 | 8.8 ± 9.7 | 7.4 ± 4.3 |
| 60 | 9.2 ± 7.4 | 4.4 ± 2.7 |
| 90 | 14.0 ± 9.1 | 12.1 ± 5.5 |
| 120 | 17.4 ± 9.9 | 10.0 ± 5.2 |
| 150 | 13.2 ± 10.5 | 14.2 ± 10.7 |
| 180 | 12.1 ± 6.2 | 8.0 ± 2.4 |

EXAMPLE 15

Caco-2 cells (a cell-line derived from human colon adenocarcinoma) were grown as a confluent mono-layer on the surface of a porous membrane (pore size 0.4 µm, surface area 0.33 cm$^2$) separating two aqueous compartments, the upper compartment filled with 200 µl of culture medium, and the lower compartment containing 600 µl. Electrical resistance across the mono-layer was measured using an epithelial voltohmeter connected to electrodes inserted into the medium on either side of the mono-layer in the upper and lower compartments. This trans-epithelial electrical resistance (TEER) was measured immediately before, and 15 minutes after the addition of aromatic alcohols to the upper compartment (see Table 6 below). Four replicates were employed for each compound, whose concentrations are shown in the table. Use of the compounds diluted two to four-fold below those concentrations shown eliminates the falls in electrical resistance observed. Fall in TEER is considered indicative of the appearance of aqueous channels between cells, and is evidence that the mechanism of action of the aromatic alcohols tested, in exerting their absorption enhancing activity, is via opening or loosening of tight junctions between intestinal cells.

TABLE 6

| Agent | Concentration (µl/ml) | TEER (ohm · cm$^2$) Before addition | TEER (ohm · cm$^2$) 15 minutes after |
|---|---|---|---|
| Phenyl ethanol | 20 | 480.5 ± 30.2 | −2.3 ± 4.7 |
| Benzyl alcohol | 40 | 447.2 ± 76.9 | −1.6 ± 3.2 |
| Phenoxy ethanol | 20 | 471.1 ± 22.4 | 8.0 ± 2.6 |

The invention claimed is:

1. A composition for oral administration which consists of an enteric capsule capable of withstanding transit through the stomach, containing a mixture comprising:
   (a) an active principal which is a polypeptide or a protein, and
   (b) at least 25% by weight of a hydrophilic aromatic alcohol absorption enhancer, wherein the enteric capsule becomes permeable at a pH from 5.5 to 7, and wherein the composition is free of glycyrrhizinate and glycyrrhizinic acid.

2. A composition according to claim 1, wherein the mixture comprising the active principal and hydrophilic aromatic alcohol absorption enhancer is substantially anhydrous.

3. A composition according to claim 2, wherein the mixture contained in the capsule comprises less than 5% water by weight.

4. A composition according to claim 1, wherein the hydrophilic aromatic alcohol absorption enhancer is a compound having a 5- or 6-membered aromatic alicyclic or heterocyclic ring which is unsubstituted or substituted by one or more halogen atoms or $C_{1-4}$ alkyl, $C_{1-4}$ alkoxy, $C_{1-4}$ alkylthio, or $C_{2-4}$ alkenyl groups; and having at least one hydroxyl group attached either to the ring directly or to the substituent groups on the ring.

5. A composition according to claim 4, wherein the hydrophilic aromatic alcohol absorption enhancer is selected from phenoxyethanol, benzyl alcohol and phenoxyethanol.

6. A composition according to claim 1, wherein the mixture contained in the capsule is in the form of a solution or a microparticulate dispersion.

7. A composition according to claim 1, wherein the mixture contained in the capsule comprises one or more agents which assist in solubilizing the active principal in the hydrophilic aromatic alcohol.

8. A composition according to claim 7, wherein the agent which assists in solubilizing the active principal is an amphiphile.

9. A composition according to claim 8, wherein the amphiphile is chosen from block co-polymers, bile salts and amphiphilic polymers.

10. A composition according to claim 9, wherein the amphiphile is chosen from cholate, glycholate, deoxycholate, glycodeoxycholate, chenodeoxycholate, taurodeoxycholate, ursodeoxycholate, fusidate and polyvinyl pyrrolidone.

11. A composition according to claim 8, wherein the amphiphile is chosen from polyoxyethylene 40 monostearate, polyoxyethylene 20 cetyl ether and polysorbate 80.

12. A method for preparing a composition according to claim 8, which method comprises co dissolving the active principal and the amphiphile in an aqueous phase and removing water and dissolving the resulting water-free complex in an hydrophilic aromatic alcohol absorption enhancer.

13. A method according to claim 12, where water is removed by lyophilising, spray-drying or by filtration of a precipitate.

14. A composition according to claim 1, wherein the active principal is calcitonin obtained from human, plant, animal, bacterial or fungal sources, which calcitonin is extracted from natural sources, prepared as a recombinant or chemically synthesised.

15. A composition according to claim 1, wherein the active principal is insulin obtained from human, plant, animal, bacterial or fungal sources, which insulin is extracted from natural sources, prepared as a recombinant or chemically synthesised.

16. A composition according to claim 1, wherein the hydrophilic aromatic alcohol is the sole absorption enhancer in the composition.

17. A composition for oral administration which consists of an enteric capsule capable of withstanding transit through the stomach, containing a mixture comprising:
 (a) an active principal which is a polypeptide or a protein, and
 (b) at least 25% by weight of a hydrophilic aromatic alcohol absorption enhancer as the sole absorption enhancer in the composition, wherein the enteric capsule becomes permeable at a pH from 5.5 to 7.

18. A composition according to claim 17, wherein the mixture comprising the active principal and hydrophilic aromatic alcohol absorption enhancer is substantially anhydrous.

19. A composition according to claim 18, wherein the mixture contained in the capsule comprises less than 5% water by weight.

20. A composition according to claim 17, wherein the hydrophilic aromatic alcohol absorption enhancer is a compound having a 5- or 6-membered aromatic alicyclic or heterocyclic ring which is unsubstituted or substituted by one or more halogen atoms or $C_{1-4}$ alkyl, $C_{1-4}$ alkoxy, $C_{1-4}$ alkylthio, or $C_{2-4}$ alkenyl groups; and having at least one hydroxyl group attached either to the ring directly or to the substituent groups on the ring.

21. A composition according to claim 20, wherein the hydrophilic aromatic alcohol absorption enhancer is selected from phenoxyethanol, benzyl alcohol and phenoxyethanol.

22. A composition according to claim 17, wherein the mixture contained in the capsule is in the form of a solution or a microparticulate dispersion.

23. A composition according to claim 17, wherein the mixture contained in the capsule comprises one or more agents which assist in solubilizing the active principal in the hydrophilic aromatic alcohol.

24. A composition according to claim 23, wherein the agent which assists in solubilizing the active principal is an amphiphile.

25. A composition according to claim 24, wherein the amphiphile is chosen from block co-polymers, bile salts and amphiphilic polymers.

26. A composition according to claim 25, wherein the amphiphile is chosen from cholate, glycholate, deoxycholate, glycodeoxycholate, chenodeoxycholate, taurodeoxycholate, ursodeoxycholate, fusidate and polyvinyl pyrrolidone.

27. A composition according to claim 24, wherein the amphiphile is chosen from polyoxyethylene 40 monostearate, polyoxyethylene 20 cetyl ether and polysorbate 80.

28. A method for preparing a composition according to claim 24, which method comprises co dissolving the active principal and the amphiphile in an aqueous phase and removing water and dissolving the resulting water-free complex in an hydrophilic aromatic alcohol absorption enhancer.

29. A method according to claim 28, where water is removed by lyophilising, spray-drying or by filtration of a precipitate.

30. A composition according to claim 17, wherein the active principal is calcitonin obtained from human, plant, animal, bacterial or fungal sources, which calcitonin is extracted from natural sources, prepared as a recombinant or chemically synthesised.

31. A composition according to claim 17, wherein the active principal is insulin obtained from human, plant, animal, bacterial or fungal sources, which insulin is extracted from natural sources, prepared as a recombinant or chemically synthesised.

32. A composition according to claim 17, which is free of glycyrrhizinate and glycyrrhizinic acid.

* * * * *